United States Patent [19]
Pagé et al.

[11] Patent Number: 6,002,025
[45] Date of Patent: Dec. 14, 1999

[54] METHOD FOR THE PURIFICATION OF TAXANES

[75] Inventors: Michel Pagé, Québec; Marie-Josée Perron, Sainte-Foy, both of Canada

[73] Assignee: BCM Developement Inc., Quebec, Canada

[21] Appl. No.: 09/256,920

[22] Filed: Feb. 24, 1999

[51] Int. Cl.$^6$ .................................................. C07D 305/14
[52] U.S. Cl. ........................................... 549/510; 549/511
[58] Field of Search ...................... 549/510, 511

[56] References Cited

U.S. PATENT DOCUMENTS

| | | | |
|---|---|---|---|
| 4,876,399 | 10/1989 | Holton et al. | 568/817 |
| 4,924,011 | 5/1990 | Denis et al. | 549/510 |
| 4,960,790 | 10/1990 | Stella et al. | 514/449 |
| 5,015,774 | 5/1991 | Suekane et al. | 564/475 |
| 5,334,732 | 8/1994 | Murray et al. | 549/510 |
| 5,412,116 | 5/1995 | Murray et al. | 549/379 |
| 5,420,337 | 5/1995 | Patel et al. | 560/41 |
| 5,549,830 | 8/1996 | Carver et al. | 210/641 |
| 5,602,272 | 2/1997 | Li et al. | 560/39 |
| 5,654,448 | 8/1997 | Pandey et al. | 549/510 |
| 5,675,025 | 10/1997 | Sisti et al. | 549/510 |
| 5,688,977 | 11/1997 | Sisti et al. | 549/510 |
| 5,750,737 | 5/1998 | Sisti et al. | 549/510 |
| 5,767,297 | 6/1998 | Mandai et al. | 549/510 |
| 5,808,113 | 9/1998 | Murray et al. | 549/510 |
| 5,817,867 | 10/1998 | Li et al. | 562/401 |

OTHER PUBLICATIONS

Witherup, et al., *J. Liq. Chromatography*, 12(11):2117–2132 (1989).

Wickremesinhe, et al., *J. Liq. Chromatography*, 16(15):3263–3274 (1993).

Richheimer, et al., *Analytical Chem.*, 64(20):2323–2326 (1992).

Rao, et al., *Pharmaceutical Research*, 12(7):1003–1010 (1995).

*Primary Examiner*—Ba K. Trinh
*Attorney, Agent, or Firm*—Ostrolenk, Faber, Gerb & Soffen, LLP

[57] ABSTRACT

Taxanes are purified by chromatographic separation using a phenylalkyl chromatographic resin, wherein the alkyl portion of the phenylalkyl is a $C_4$–$C_{10}$ moiety. Taxanes such as paclitaxel, 10-deacetyltaxol, 7-epi-taxol, cephalomannine, baccatin III, baccatin V, 7-epi-DAB, 10-deactylbaccatin III ("DAB") and 9-dihydro-13-acetylbaccatin III ("DHB") and others may be purified. In accordance with the invention, taxanes are separated from each other and from other impurities common to crude taxane samples.

21 Claims, 10 Drawing Sheets

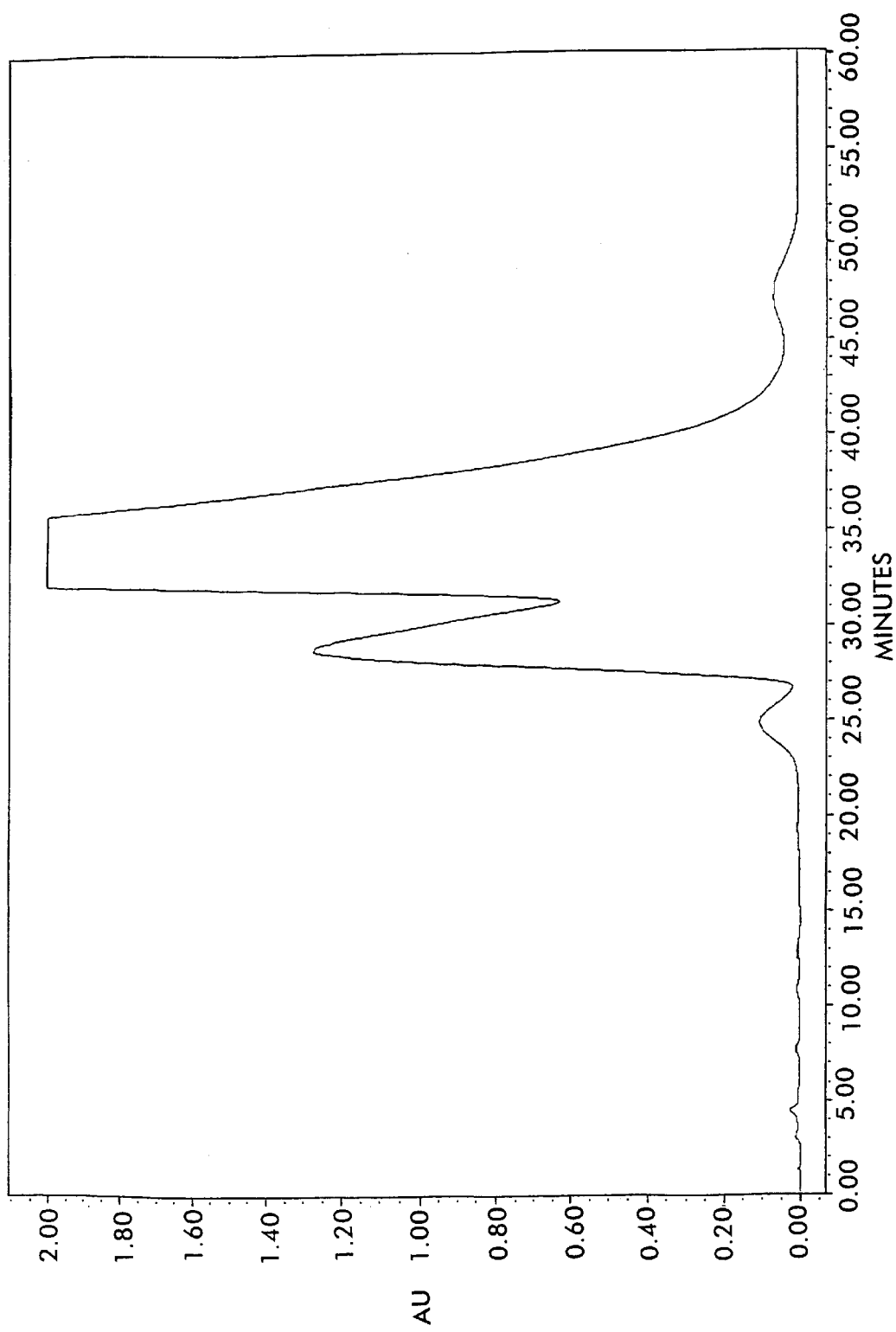

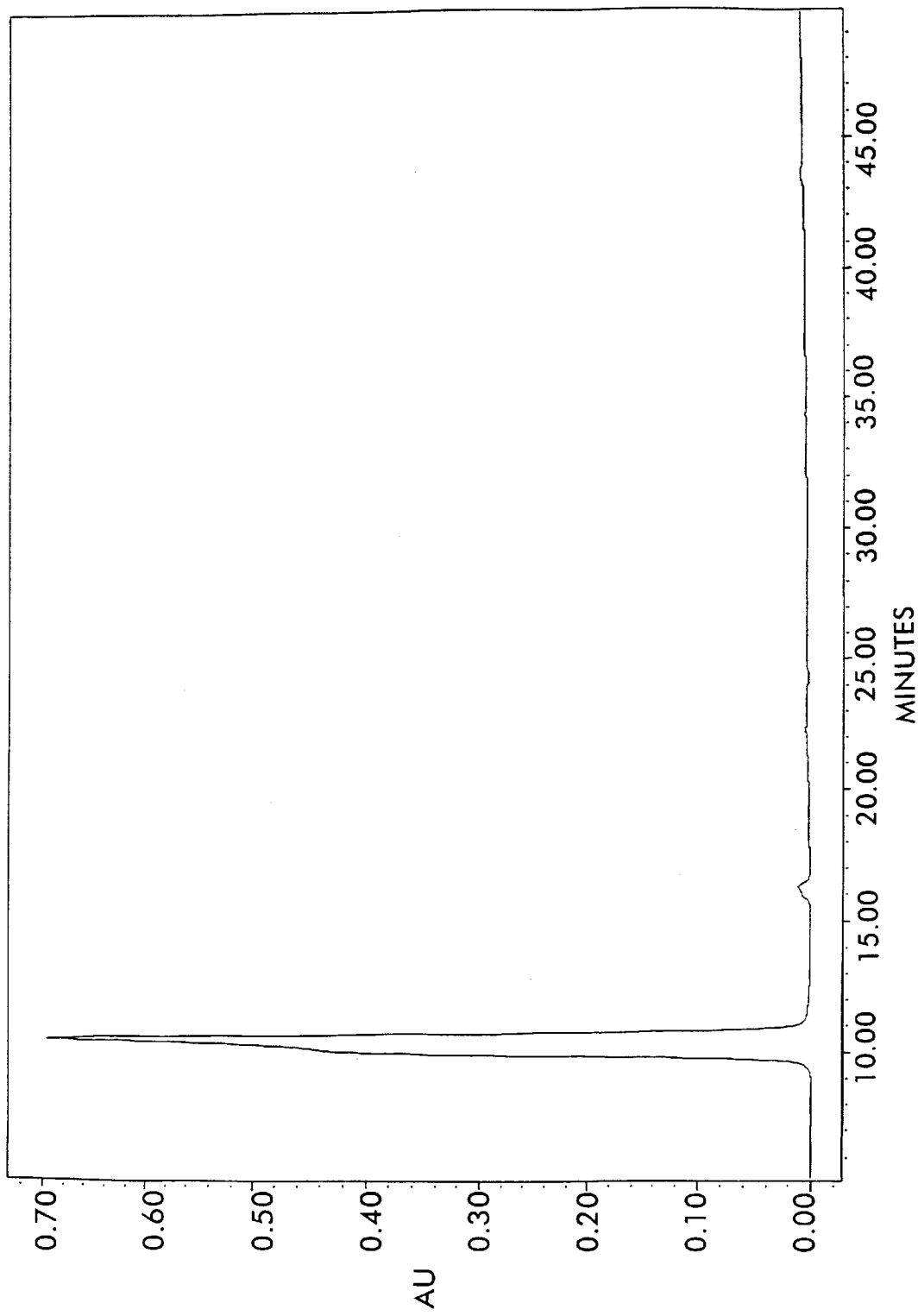

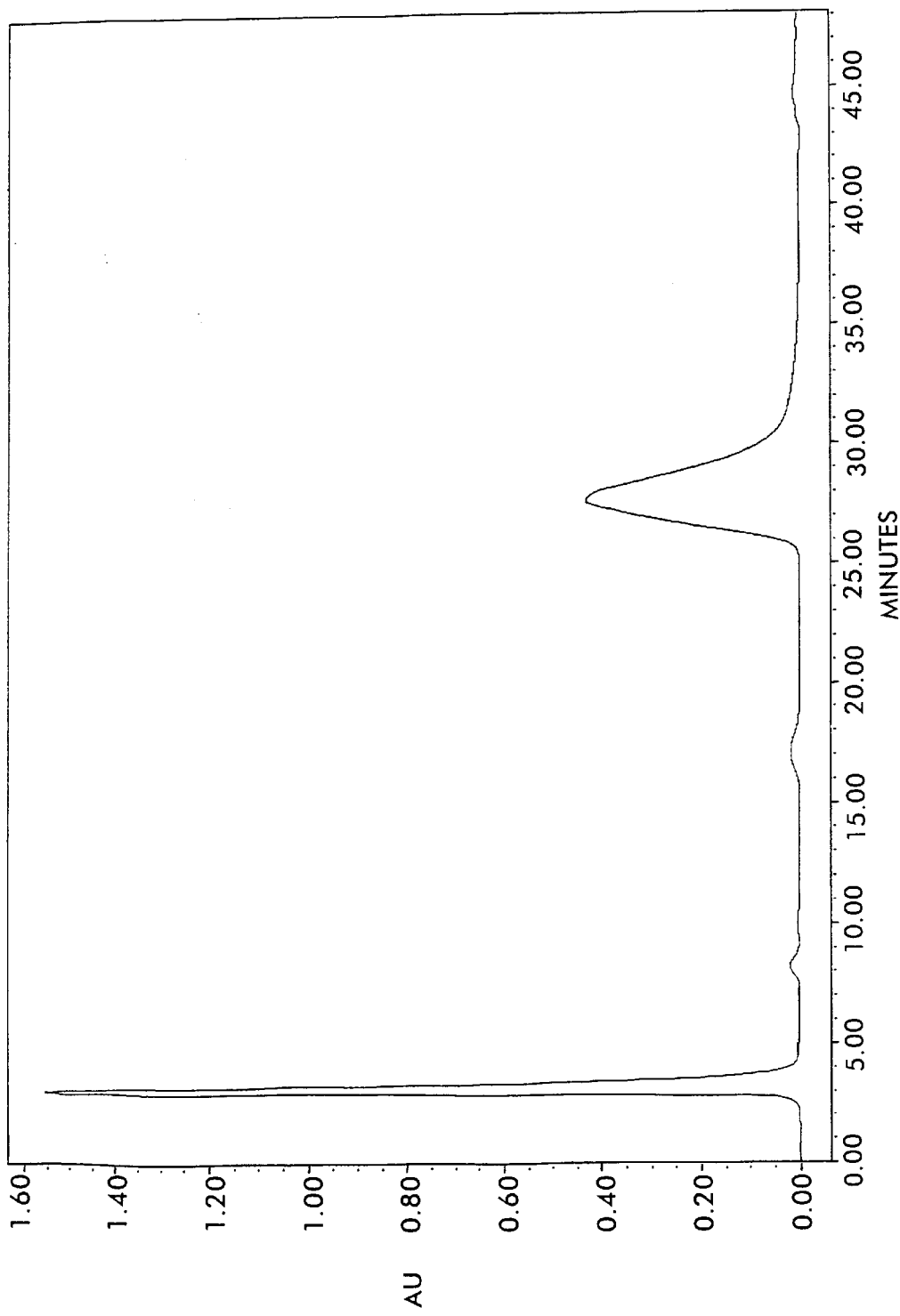

METHOD FOR THE PURIFICATION OF TAXANES

FIELD OF THE INVENTION

This invention relates to the chromatographic purification of taxanes using certain phenylalkyl resins having from 4–10 carbon atoms on the alkyl portion of the phenylalkyl moiety. In particular, some embodiments of the invention employ reverse-phase chromatography using a phenylhexyl column connected to a suitable HPLC preparative system. Highly pure taxanes (purity over 98.5%) have been achieved in a single chromatography step starting with crude material whose purity was in excess of 50% by weight, although lesser purity crude samples may also benefit from the invention. All of the foregoing percentages are weight percentages relative to all other materials in the crude mixture, but excluding any chromatography solvents or solvents used to extract crude taxanes from their original source.

RELATED ART

Numerous taxanes are known to be useful for pharmaceutical purposes. For example, paclitaxel is a natural product that may be extracted from the bark of the Pacific yew (*Taxus brevifolia*) and other members of the Taxacae family including the yew of Canada (*Taxus canadensis*) found in Gaspesia, eastern Canada and *Taxus baccata* found in Europe (whose needles contain paclitaxel and analogs, and which hence provide a renewable source of paclitaxel and derivatives). The crude extract was tested for the first time during the 1960's, and its active principle (paclitaxel) was isolated in 1971 by Wani et al., who at the same time identified its chemical structure. Paclitaxel showed a wide range of activity over melanoma cells, leukemia, various carcinomas, sarcomas and non-Hodgkin lymphomas, as well as a number of solid tumors in animals. It is presently used in the therapy of refractory ovarian cancer and breast cancer. Clinical studies suggest that its use might be extended to other types of cancers such as lung cancer. Its unique mechanism of action makes it different from other microtubule blockers. Unlike other drugs inhibiting mitosis by interaction with microtubules (e.g. colchicin, vincristin and podophyllotoxin), paclitaxel is not believed to prevent tubulin assembly, but rather to accelerate tubulin polymerization and stabilize assembled microtubules, leading ultimately to cell death.

Taxol™ is a commercial pharmaceutical product whose active ingredient is paclitaxel. Semisynthesis allows scientists to chemically modify naturally occurring taxanes in order to get more effective and soluble drugs. That process led to the creation of Taxotere™, commercialized by Rhone-Poulenc Rorer. The synthesis of Taxotere™ involves a natural taxane, 10-deacetyl baccatin III (DAB). Other drugs involving taxanes are being biologically evaluated (see, e.g. PCT Patent Application Nos. WO95/13270, WO95/33736, WO96/32387, and WO97/23473). Abbott Laboratories synthesized a new drug from 9-dihydro-13-acetylbaccatin III (DHB), isolated from *Taxus canadensis*. In the development of alternative processes for producing paclitaxel, Sisti et al. (U.S. Pat. No. 5,675,025) developed a semisynthesis of paclitaxel from baccatin III. Multistep taxane purification methods (described in more detail infra) are known in the art. Phenyl columns have been reported for purification of some taxanes by Witherup, et al., *J. Liq. Chromatography*, 12(11):2117–2132 (1989). Applicant believes these phenyl columns to include phenylpropyl moieties. Purification of taxanes from each other and from other contaminants with which they are frequently associated can be difficult. There is believed to be a significant need in the art for good taxane purification techniques.

SUMMARY OF THE INVENTION

It is accordingly an object of the present invention to provide a purification technique for providing good separation of taxanes from each other.

It is another object of the invention to provide good separation of taxanes from contaminants with which taxanes are frequently associated such as carotenoids, chlorophyles, xanthophyles, long chain carbon compounds, waxes and pigments.

It is another object of the invention to provide a taxane purification technique that may be used as a significant purity-enhancing step of a larger multi-step taxane purification technique.

It is another object of the invention to provide high purity taxanes.

It is another object of the invention to provide high purity taxanes for use as pharmaceutical agents or as precursors to other pharmaceutical or commercial agents.

These and other objects may be achieved by practice of the invention described herein. In one embodiment, the invention provides a method for purifying a taxane, said method comprising the steps of:

(A) obtaining a crude taxane sample;

(B) subjecting said sample to chromatographic separation by passing said sample through a chromatographic column containing a phenylalkyl resin, wherein the alkyl portion of said phenylalkyl has from 4 to 10 carbon atoms; and thereafter (C) collecting a fraction of an eluant of said column containing said taxane.

In another embodiment, the invention provides a method for purifying a taxane, said method comprising the steps of:

(A) obtaining a crude taxane sample comprising said taxane at a concentration higher than 50% (by weight of said sample excluding extraction or chromatography solvents);

(B) solubilizing said sample;

(C) injecting said solubilized sample into a phenylhexyl chromatographic column connected to an HPLC preparative system;

(D) performing chromatographic separation by passing, through said column, solvents that include both organic and aqueous components;

(E) collecting a fraction of an eluant of said column containing said taxane;

(F) removing the solvent.

Taxanes are a class of compounds characterized by the three-ring nucleus shown below being part of their molecular structure:

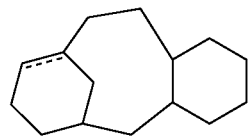

The dotted line in the above structure is an optional pi bond. Because the present invention provides good separation of taxanes from each other and from common taxane contaminants, any taxane of interest (whether one presently known to have commercial value or one subsequently discovered to have commercial value) is expected to benefit from purification in accordance with the present invention.

Several classes and types of taxanes are discussed in more detail below. Common impurities to be removed in accordance with the invention include but are not limited to vegetal pigments such as carotenoids, chlorophyles, xanthophyles, long chain carbon compounds, waxes and pigments or any organic or inorganic chemicals from the source. Other common impurities are other taxanes identified in Table I below where $R_1$–$R_{17}$ are substituents as shown on the molecular structure below:

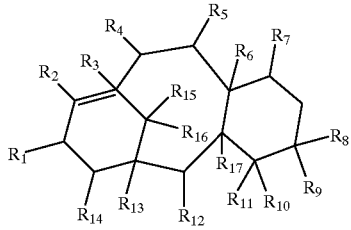

TABLE 1

| Compound | $R_1$ | $R_2$ | $R_3$ | $R_4$ | $R_5$ | $R_6$ | $R_7$ | $R_8 R_{17}$ | $R_9 R_{10}$ | $R_{11}$ | $R_{12}$ | $R_{13}$ | $R_{14}$ | $R_{15}$ | $R_{16}$ |
|---|---|---|---|---|---|---|---|---|---|---|---|---|---|---|---|
| paclitaxel | tax | $CH_3$ | H | β-acetyloxy | =O | β-$CH_3$ | β-OH | H | oxetane | α-acetyloxy | α-benzoloxy | β-OH | H | $CH_3$ | $CH_3$ |
| 10-deacetyl-cephalomannine | ceph | $CH_3$ | H | β-OH | =O | β-$CH_3$ | β-OH | H | oxetane | α-acetyloxy | α-benzoloxy | β-OH | H | $CH_3$ | $CH_3$ |
| 7-epitaxol | tax | $CH_3$ | H | β-acetyloxy | =O | β-$CH_3$ | α-OH | H | oxetane | α-acetyloxy | α-benzoloxy | β-OH | H | $CH_3$ | $CH_3$ |
| 10-deacetyl-7-epitaxol | tax | $CH_3$ | H | β-OH | =O | β-$CH_3$ | α-OH | H | oxetane | α-acetyloxy | α-benzoloxy | β-OH | H | $CH_3$ | $CH_3$ |
| 7-epi-cephalomannine | ceph | $CH_3$ | H | β-acetyloxy | =O | β-$CH_3$ | α-OH | H | oxetane | α-acetyloxy | α-benzoloxy | β-OH | H | $CH_3$ | $CH_3$ |
| baccatin III | α-OH | $CH_3$ | H | β-acetyloxy | =O | β-$CH_3$ | β-OH | H | oxetane | α-acetyloxy | α-benzoloxy | β-OH | H | $CH_3$ | $CH_3$ |
| 10-deacetyl baccatin III | α-OH | $CH_3$ | H | β-OH | =O | β-$CH_3$ | β-OH | H | oxetane | α-acetyloxy | α-benzoloxy | β-OH | H | $CH_3$ | $CH_3$ |
| cephalomannine | ceph | $CH_3$ | H | β-acetyloxy | =O | β-$CH_3$ | β-OH | H | oxetane | α-acetyloxy | α-benzoloxy | β-OH | H | $CH_3$ | $CH_3$ |
| 10-deacetyl taxol | tax | $CH_3$ | H | β-OH | =O | β-$CH_3$ | β-OH | H | oxetane | α-acetyloxy | α-benzoloxy | β-OH | H | $CH_3$ | $CH_3$ |
| 7-xylosyl taxol | tax | $CH_3$ | H | β-acetyloxy | =O | β-$CH_3$ | β-xylosyl | H | oxetane | α-acetyloxy | α-benzoloxy | β-OH | H | $CH_3$ | $CH_3$ |
| 7-xylosyl-cephalomannine | ceph | $CH_3$ | H | β-acetyloxy | =O | β-$CH_3$ | β-xylosyl | H | oxetane | α-acetyloxy | α-benzoloxy | β-OH | H | $CH_3$ | $CH_3$ |
| taxagifine | =O | α-$CH_3$ | β-OH | β-acetyloxy | α-acetyloxy | β-$CH_3$ | β-acetyloxy | H | α-cinnamoyloxy | methylene (=$CH_2$) | α-acetyloxy | β-H | H | cyclo | α-$CH_3$ |
| δ-benzoyloxy-taxagifine | =O | α-$CH_3$ | β-OH | β-acetyloxy | α-acetyloxy | β-benzoyloxymethyl | β-acetyloxy | H | α-cinnamoyloxy | methylene (=$CH_2$) | α-acetyloxy | β-H | H | cyclo | α-$CH_3$ |
| 9-acetyloxy-taxusin | α-acetyloxy | $CH_3$ | H | β-acetyloxy | α-acetyloxy | β-$CH_3$ | H | H | α-acetyloxy | methylene (=$CH_2$) | H | H | H | $CH_3$ | $CH_3$ |
| 9-hydroxy-taxusin | α-acetyloxy | $CH_3$ | H | β-acetyloxy | α-OH | β-$CH_3$ | H | H | α-acetyloxy | methylene (=$CH_2$) | H | H | H | $CH_3$ | $CH_3$ |
| taxane 1a | tax | $CH_3$ | H | =O | =O | β-$CH_3$ | α-OH | H | oxetane | α-acetyloxy | α-benzoloxy | β-OH | H | $CH_3$ | $CH_3$ |
| taxane 1b | taxsub | $CH_3$ | H | =O | =O | β-$CH_3$ | α-OH | H | oxetane | α-acetyloxy | α-benzoloxy | β-OH | H | $CH_3$ | $CH_3$ |
| taxane 1c | taxsub | $CH_3$ | H | =O | =O | β-$CH_3$ | α-acetyloxy | H | oxetane | α-acetyloxy | α-benzoloxy | β-OH | H | $CH_3$ | $CH_3$ |
| taxane 1d | α-acetyloxy | $CH_3$ | H | β-acetyloxy | α-acetyloxy | β-$CH_3$ | β-acetyloxy | H | α-OH | epoxide | α-acetyloxy | β-OH | H | $CH_3$ | $CH_3$ |

TABLE 1-continued

| Compound | $R_1$ | $R_2$ | $R_3$ | $R_4$ | $R_5$ | $R_6$ | $R_7$ | $R_8 R_{17}$ | $R_9 R_{10}$ | $R_{11}$ | $R_{12}$ | $R_{13}$ | $R_{14}$ | $R_{15}$ | $R_{16}$ |
|---|---|---|---|---|---|---|---|---|---|---|---|---|---|---|---|
| 7-epibaccatin III | α-OH | $CH_3$ | H | β-acetyloxy | =O | β-$CH_3$ | α-OH | H | oxetane | α-acetyloxy | α-benzoloxy | β-OH | H | $CH_3$ | $CH_3$ |

In the Table above,

"ceph" denotes

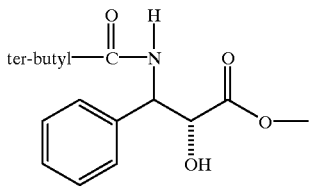

"tax" denotes

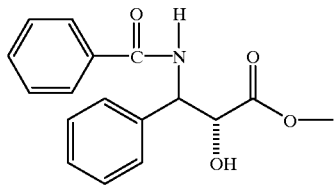

"taxsub" denotes

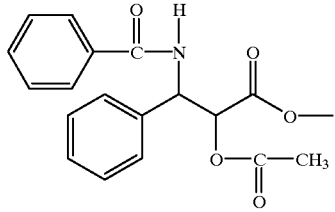

"xylosyl" denotes

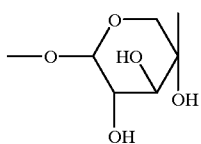

"α" denotes the stereoposition

of a moiety below the plane of the taxane ring structure as defined herein.

"β" denotes the stereoposition

of a moiety above the plane of the taxane ring structure as defined herein.

"oxetane" denotes the moiety

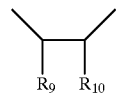

which is

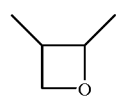

as a result of a covalent bond between $R_9$ and $R_{10}$.

"cyclo" denotes the cyclic group formed by bonding the group

to the third ring of the taxane structure as follows:

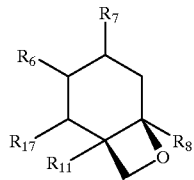

"epoxide" denotes the moiety

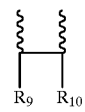

which is

as a result of $R_9$ and $R_{10}$ both being the same oxygen atom

Although Table 1 includes taxane impurities that are frequently undesirable and to be removed when other taxanes are being purified, the invention could also be useful to provide high purity to the taxanes of Table 1, should any such taxanes be of commercial value. In other words, a taxane may be either purified by removal of other taxanes, or may itself be removed in accordance with the invention. Because the invention separates taxanes from each other, a plurality of commercially desirable taxanes may be purified from a single crude source in accordance with the invention.

BRIEF DESCRIPTION OF THE DRAWINGS

FIG. 3A is a chromatogram of 65% paclitaxel used as a crude material in Example 1 herein.

FIG. 4B is a quality control chromatogram after completion of the Example 2 purification in accordance with the invention.

FIG. 5A is the quality control chromatogram of 87% DHB used as crude material in Example 3 herein.

DETAILED DESCRIPTION OF THE INVENTION

Figure 1:
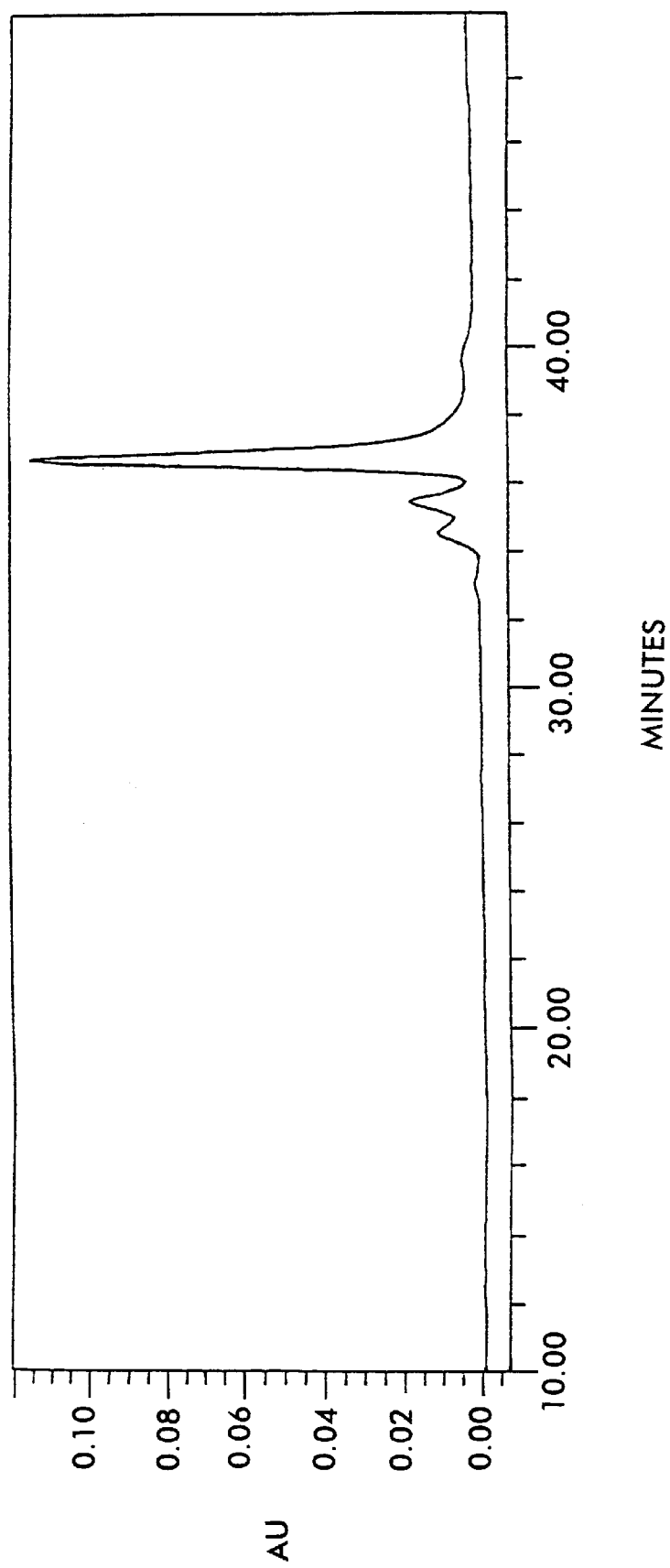
FIG. 1 is a quality control chromatogram (procedure explained in detail infra) of paclitaxel purified in a column using silica resin, instead of the phenylhexyl resin of the present invention. Numerous impurities are shown. The maximum purity obtained with this resin was only 81%, as opposed to the 98.5% purities applicants have achieved using resins of the invention.
Figure 2:
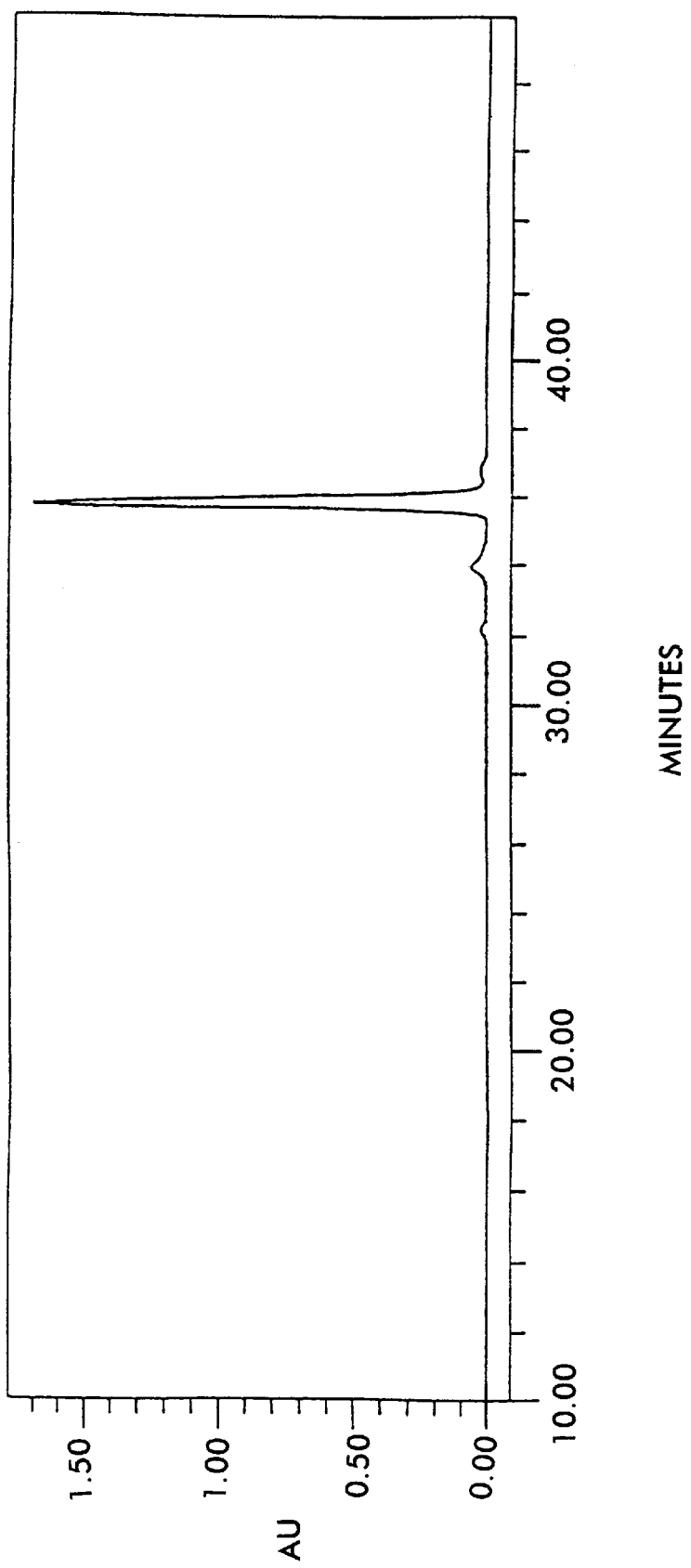
FIG. 2 is a quality control chromatogram of paclitaxel purified using a column having a C-18 matrix (alkyl chain of 18 carbons) instead of the phenylalkyl resins of the invention. Impurities are shown. Applicant achieved only a maximum of 93% purity using this resin, as opposed to the 98.5% purity obtained using resins of the invention.

Sources of Taxanes and Initial Preparation of a Crude Taxane Sample

Sources of taxanes include vegetal cell culture (U.S. Pat. Nos. 5,019,504; 5,637,484; 5,665,576; and PCT Patent Application No. WO93/23555), production by fungus (U.S. Pat. No. 5,322,779) and production by bacteria (U.S. Pat. No. 5,561,055).

Paclitaxel and other taxanes may also be isolated from the bark and needles of different Taxus species. The process involves the drying of vegetal clippings, which may include bark, branches, twigs, needles, seeds, fruits and roots of the yew. The process of extraction differs among users. In U.S. Pat. No. 5,475,120, several methods are described. One such method used by Polysciences Inc. includes the following steps:

1. The dried ground bark is extracted with either methanol or ethanol and the combined extracts concentrated;
2. The concentrate is then extracted with dichloromethane and the solvent evaporated to yield a powder;
3. The powder is stirred with a mixture of acetone and ligroin, and filtered to remove insoluble matter.
4. The filtrate which contains paclitaxel is concentrated, dissolved in 30% acetone in ligroin, and applied to a column of Florisil;
5. The paclitaxel fraction from the column is purified by crystallization twice;
6. The crystalline paclitaxel is further subjected to chromatography on a silica column. In this step, the closely related analog, cephalomannine, is separated from taxol; and
7. The purified taxol obtained from the column is crystallized twice.

Another method published by Miller and co-workers, Miller, R. W., et al., *Antileukemic alkaloids from Taxus wallichiana Zucc., J. Org. Chem.*, 46(7):1469–1474 (1981), involves the following steps:

1. Extraction of the plant and concentration of the extract to a solid;
2. Defatting by partition between water and hexane;
3. Extraction with chloroform and concentration;
4. Silica column chromatography;
5. A second silica chromatography;
6. Countercurrent distribution;
7. A second countercurrent distribution;
8. Preparative HPLC.

Of course, there are other methods for the purification of paclitaxel from natural sources. Those methods differ mainly in the choice of the organic solvents used in liquid extraction, in the crystallization step or the method used to remove pigments. As an example, our process can be used in replacement of either step 4 of the method of Polysciences above, or of step 8 of the method of Miller and co-workers. While our process can be used with any crude taxane mixture, preliminary partial purification in accordance with known techniques is desirable. In preferred embodiments, a minimum purity of 50% for the selected taxane to be purified is desired. The foregoing is a weight percentage relative to all of the crude sample, but excluding extraction solvents or chromatography solvents.

Our process involves the following steps.

1. Solubilizing the partly purified taxane powder in an appropriate solvent for injection on preparative HPLC;
2. Perform a chromatography on a phenylhexyl column using appropriate solvents;
3. Collect the appropriate taxane peak;
4. Evaporate in vacuo the taxane peak to eliminate the organic solvent;
5. Crystallization and lyophilization of the taxane concentrate.

This single step process yields a taxane with a purity over 98.5%.

Taxanes that are expected to benefit from purification in accordance with the present invention include synthetic or semi-synthetic taxanes as well as natural taxanes (e.g., derived from a vegetal, microbial or fungal source). Like taxanes from vegetal sources, taxanes derived from bacterial or fungal fermentation are expected to exist as a mixture of taxanes which will benefit from the taxane separation provided by the present invention.

Any natural sources containing taxanes may be used for this process. These sources can be from vegetal origin (either from plant clipping or vegetal cell culture) or from bacterial origin as described in U.S. Pat. No. 5,561,055 or from fungal origin as described in PCT Patent Application No. WO96/32490 and in publications by Strobel and co-workers. The preferred sources are from partially purified taxanes from vegetal grounded material of Taxus genus such as: *Taxus brevifolia, Taxus canadensis, Taxus baccata, Taxus chinensis, Taxus cuspidata,* Taxus X media cultivars, *Taxus yunnanensis, Taxus floridana* and *Taxus wallichiana*. The most preferred material can be selected from the group consisting of *Taxus brevifolia, Taxus chinensis, Taxus canadensis* and *Taxus yunnanesis*.

The process may be applied to a partially purified taxane mixture from the above sources having a purity of at least 50% for the selected taxane to be purified. The most preferred taxanes to be purified are paclitaxel (active ingredient in the pharmaceutical product, TAXOL™) DAB, baccatin III and DHB, and others whose chemical structures are shown below.

carbon atoms, preferably 5–7. Phenylhexyl resins have proven especially useful as further described in the examples herein. It is believed that the alkyl portion of the phenylalkyl resin may vary from 4–10 carbon atoms in order to better separate compounds of similar chemical structure. This 4–10 carbon alkyl portion is used as a side arm to present the phenyl group thus avoiding steric hindrance. This side arm is also used as a hydrophobic moiety on the silica. The preference for 5–7 carbon alkyl portions (of the phenyl alkyl

|  | $R^1$ | $R^2$ | $R^3$ | $R^4$ |
|---|---|---|---|---|
| paclitaxel | OH | H | Ac | Ph |
| 10-deacetyltaxol | OH | H | H | Ph |
| 7-epi-taxol | H | OH | H | Ph |
| cephalomannine | OH | H | Ac | ter-butyl |

| | $R^1$ | $R^2$ | $R^3$ |
|---|---|---|---|
| baccatin III | OH | H | AC |
| DAB | OH | H | H |
| 7-epi-DAB | H | OH | Ac |

| | $R^1$ | $R^2$ |
|---|---|---|
| DHB | H | H |

The Phenylalkyl Resin

In particular, applicants have found that certain phenylalkyl chromatographic resins have good ability to separate taxanes from each other and from other contaminants with which taxanes are frequently associated (e.g., vegetal pigments such as carotenoids, chlorophyles and xanthophyles, long carbon chain compounds, waxes and other pigments). The alkyl portion of the phenylalkyl resin has from 4–10 resin) concerns the eluotropic force necessary to elute components which, in this case, is moderate. Using phenylhexyl resin applicants were able to separate cephalomannine and 7-epi-10-deacetyltaxol from paclitaxel. Cephalomannine and 7-epi-10-deacetyl taxol usually co-elute under other chromatographic conditions (for example, C-18 and silica matrix) and are difficult to separate from paclitaxel.

The phenylalkyl moiety may be linked onto any suitable chromatographic structural support including but not limited to silica. For example, a phenylhexyl resin may have the following structural configuration:

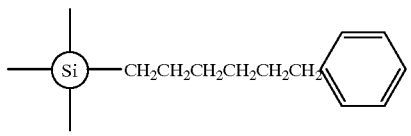

wherein the silica, other silicon-based resin, or other chromatographic support, may optionally be linked to other phenylalkyl moieties. By way of example only, three such optional points of linkage are shown on the diagram above. The composition and structure of the support may vary widely, and many such supports are known in the art.

In some embodiments, a single-step purification process of the taxane of interest by reverse-phase chromatography on a phenylalkyl column in accordance with the invention comprises the following steps:

(1) An aliquot of the crude extract (preferably containing at least 50% of the taxane to be purified) is solubilized in methanol.

(2) An appropriate amount of the solubilized extract is injected into the phenylalkyl column connected to a suitable HPLC preparative system. The amount injected varies in a known manner with the size of the column used. In the process of the example herein, the dimension of the column may vary from 25 to 100 cm in length and from 4.6 to 100 mm in diameter. The particle size ranges from 5 to 15 μm.

(3) While a ramped gradient elution program may be used, applicants have obtained good results when the taxane to be purified is separated from contaminants by an isocratic mode. Preferred isocratic modes involve methanol and water, or acetonitrile and water, or methanol, acetonitrile and water. The proportion of methanol may vary from 45 to 75%. The proportion of acetonitrile may range from 1 to 45%. The proportion of water may vary from 25 to 60%.

(4) The peak containing the taxane of interest is preferably evaporated in vacuo in order to get rid of the organic solvent. Meanwhile, the taxane starts to precipitate in the residual aqueous phase.

(5) The aqueous phase containing the taxane of interest is then preferably freeze dried.

(6) The purified taxane may then be submitted to the quality assurance protocols in place.

The quality assurance control consists of injecting 5 μg of a taxane sample of unknown purity into a curosil-PFP column (3.2 mm×250 mm, 5 μm) connected to an analytical HPLC system (Waters™ 625 LC pump, 996 photodiode array spectrophotometer, and 717plus autosampler). The following gradient elution program was used:

0 to 50 min.: acetonitrile:water (25:75) ramped to acetonitrile:water (65:35), flow rate of 0.8 ml/min.

50 to 62.5 min.: acctonitrilc:water (65:35) ramped to methanol 100%, flow rate of 0.8 ml/min.

62.5 to 67.5 min.: methanol 100%, flow rate of 0.8 ml/min.

67.5 to 70 min.: methanol 100% ramped to acetonitrilc:water (25:75), flow rate of 0.4 ml/min.

70 to 88 min.: acetonitrile:water (25:75).

The chromatography is performed at a controlled temperature of 30° C. Table 2 illustrates the retention times of common taxanes from this analytical process.

TABLE 2

Retention time of taxane standards using the analytical HPLC method

| Taxane | Retention Time |
|---|---|
| 10-deacetylbaccatin III | 10.40 min. |
| baccatin III | 18.08 min. |
| 9-dihydro-13-acetylbaccatin III | 22.00 min. |
| 10-deacetyl-7-xylosyl taxol B | 23.18 min. |
| 10-deacetyl-7-xylosyl taxol | 24.62 min. |
| taxinine M | 25.51 min. |
| 10-deacetyl-7-xylosyl taxol C | 27.34 min. |
| cephalomannine | 31.94 min. |
| 7-epi-10-deacetyltaxol | 32.94 min. |
| paclitaxel | 34.27 min. |
| taxol C | 36.38 min. |
| 7-epi-taxol | 39.14 min. |

The present invention will be more readily understood by referring to the following examples which are given to illustrate the invention rather to limit its scope.

EXAMPLE 1

Purification of paclitaxel by preparative HPLC using a phenylhexyl column with method no. 1

Figure 3B:
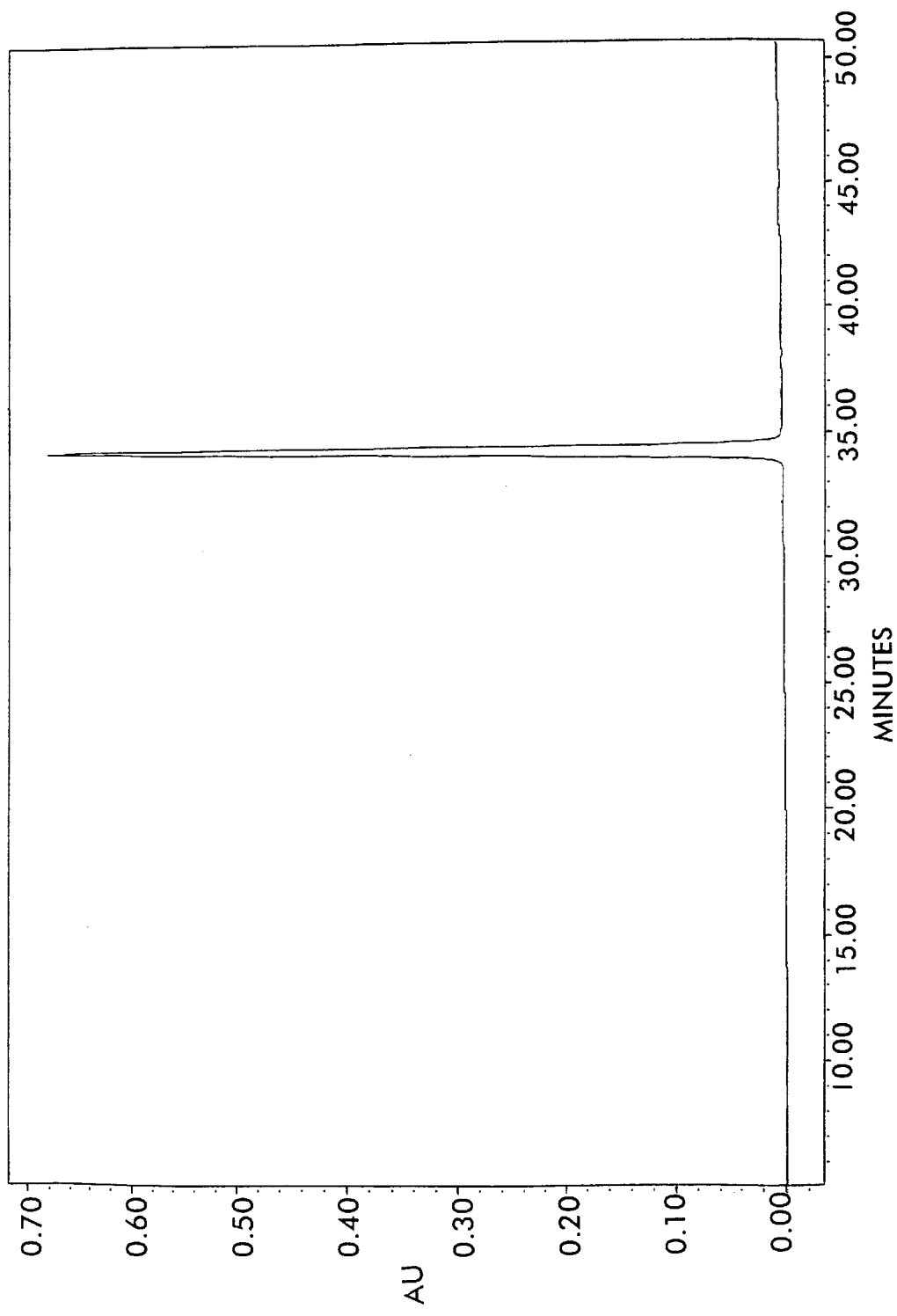
FIG. 3B is a quality control chromatogram of purified paclitaxel after completion of the Example 1 purification in accordance with the invention.

In a typical purification process, 65% paclitaxel from an Asian supplier is used as raw material. First, 300 mg of this material is solubilized in 1 ml methanol HPLC grade and manually injected into two phenylhexyl columns (Phenomenex, 21.2 mm×250 mm, 15 μm) connected in series to a preparative HPLC system (Waters, Prep LC2000). On-line monitoring of the purification process is performed at 245 nm on a tunable wavelength UV spectrophotometer (Waters, Model 486). Separation of the compounds is achieved under isocratic conditions which are methanol:water (65:35) at a flow rate of 37 ml/min. Under those conditions, paclitaxel is eluted between 31.6 and 44.6 minutes. However, the collection of paclitaxel begins at 33.7 min. and ends at 41.3 minutes. As described above, the collected peak containing paclitaxel is evaporated in vacuo and submitted to a freeze drying process. The final yield of this purification process is 60% of paclitaxel (purity over 98.5%). FIG. 3A illustrates the content of the 65% pure paclitaxel used as raw material and FIG. 3B illustrates the content of the paclitaxel submitted to our purification process. Those chromatograms clearly demonstrate the high purity of the paclitaxel resulting from this purification process.

EXAMPLE 2

Purification of DAB by preparative HPlC using a phenylhexyl column with method no. 2

Figure 4A:
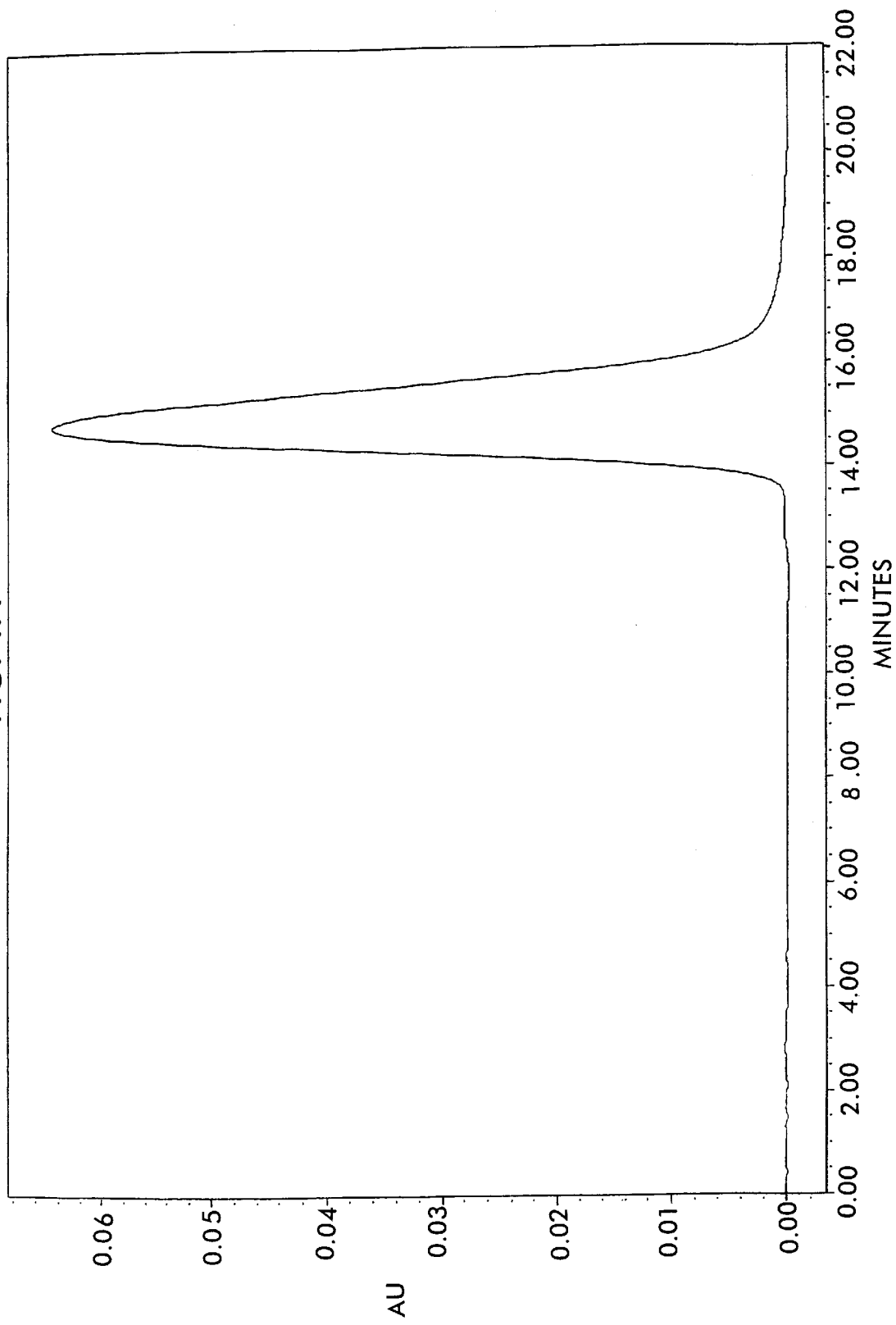
FIG. 4A is a quality control chromatogram of crude 92% pure DAB used in Example 2 herein.

In a typical purification process, DAB (92%) from a Canadian supplier is used as raw material. First, 10 mg of this material is solubilized in 1 ml methanol HPLC grade and manually injected into one phenylhexyl column ((Phenomenex, 21.2 mm×250 mm, 15 μm) connected to a preparative HPLC system (Waters, Prep LC2000). On-line monitoring of the purification process is performed at 228 nm on a tunable wavelength UV spectrophotometer (Waters, Model 486). Separation of the compounds is achieved under isocratic conditions which are methanol:water (50:50) at a flow rate of 20 ml/min. Under those conditions, DAB is eluted between 10.0 and 19.0 minutes. However, the collection of DAB begins at 12.1 min. and ends at 16.0 minutes. As described above, the collected peak containing DAB is evaporated in vacuo. The final yield of this overall purification process is 70% of DAB (purity over 98.5%). FIG. 4A illustrates the content of the 92% pure DAB used as raw material and FIG. 4B illustrates the content of the DAB submitted to our purification process. Those chromatograms clearly demonstrate the high purity of the DAB resulting from this purification process.

EXAMPLE 3

Purification of DHB by preparative HPLC using a phenylhexyl column with method no. 3

Figure 5B:
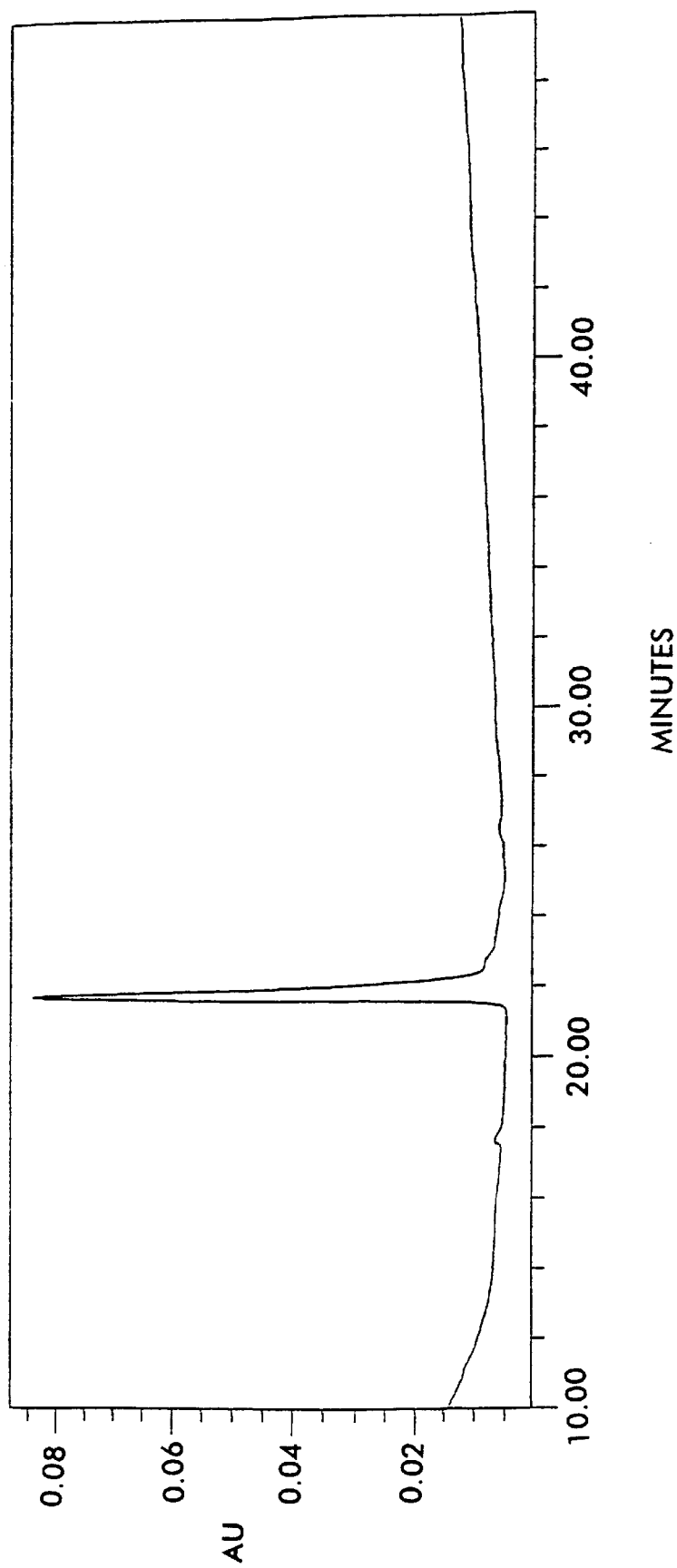
FIG. 5B is the quality control chromatogram of the same DHB after completion of the Example 3 purification in accordance with the invention.

In a typical purification process, DHB (87%) from a Canadian supplier is used as raw material. First, 10 mg of this material is solubilized in 1 ml DMSO and manually injected into one phenylhexyl column ((Phenomenex, 21.2 mm×250 mm, 15 μm) connected to a preparative HPLC system (Waters, Prep LC2000). On-line monitoring of the purification process is performed at 228 nm on a tunable wavelength UV spectrophotometer (Waters, Model 486). Separation of the compounds is achieved under isocratic conditions which are methanol:water (50:50) at a flow rate of 20 ml/min. Under those conditions, DHB is eluted between 22.0 and 38.0 minutes. However, the collection of DHB begins at 25.1 min. and ends at 32.5 minutes. As described above, the collected peak containing DHB is evaporated in vacuo. The final yield of this overall purification process is 50% of DHB (purity over 98.5%). FIG. 5A illustrates the content of the 87% pure DHB used as raw material and FIG. 5B illustrates the content of the DHB submitted to our purification process. Those chromatograms clearly demonstrate the high purity of the DHB resulting from this purification process.

EXAMPLE 4

Purification of paclitaxel by preparative HPLC using a phenylhexyl column with method no. 4

Figure 6A:
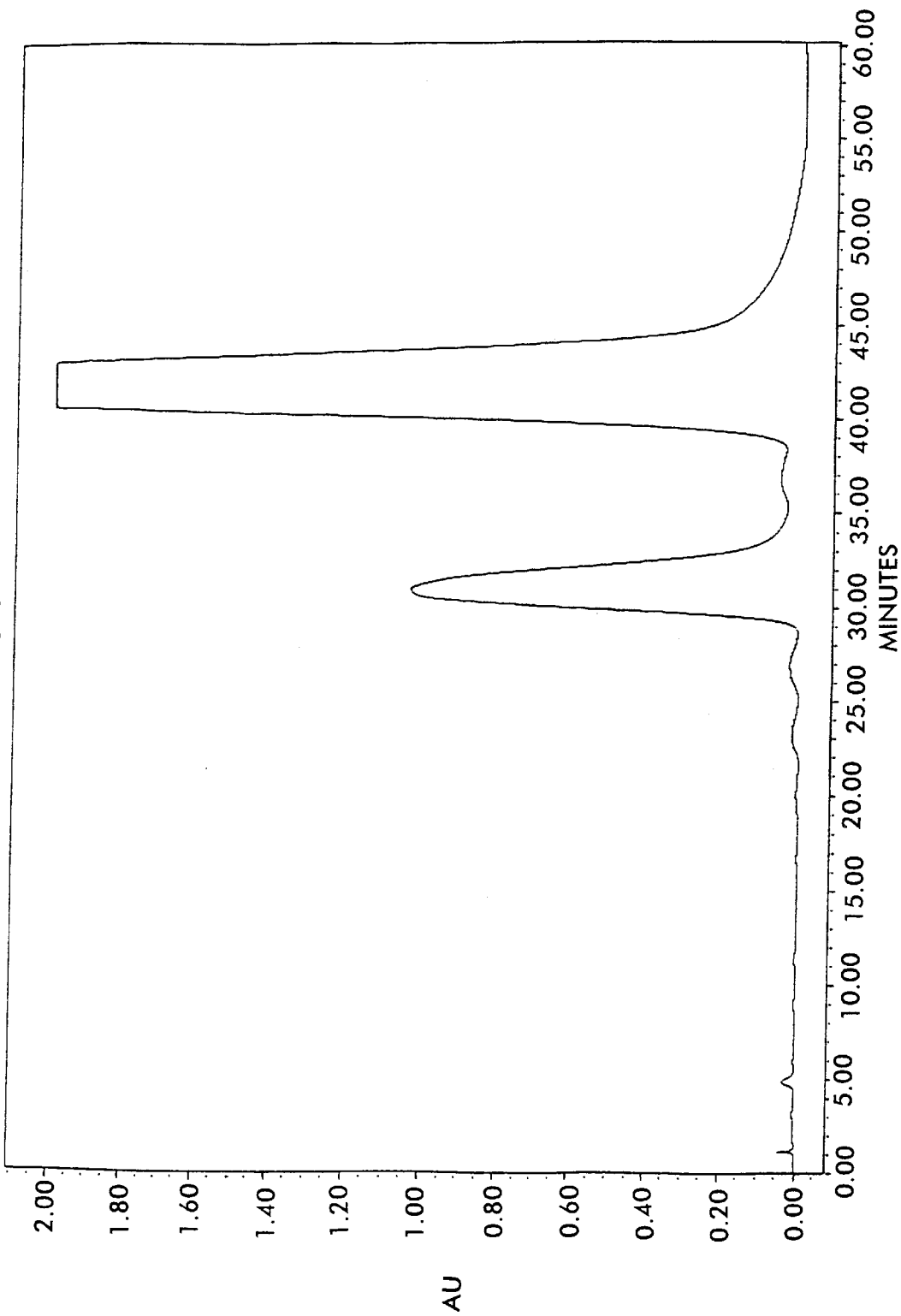
FIG. 6A is the quality control chromatogram of 65% paclitaxel used as crude material in Example 4 herein.
Figure 6B:
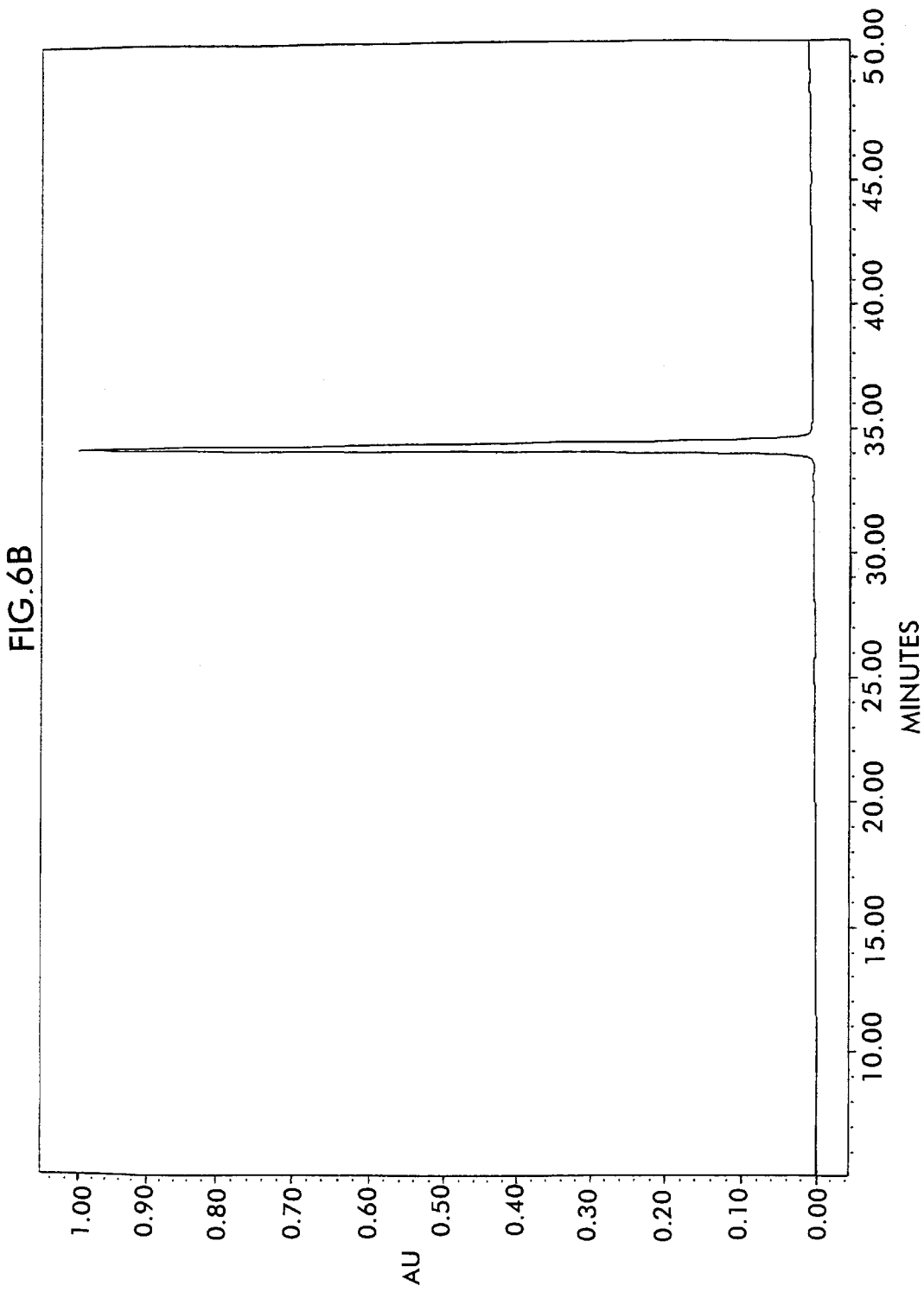
FIG. 6B is the quality control chromatogram of the same paclitaxel after completion of the Example 4 purification in accordance with the invention.

Depending on impurities in the raw material, we can use a different composition of the mobile phase. In a typical purification process, paclitaxel (65%) from an Asian supplier is used as raw material. First, 50 mg of this material is solubilized in 500 μl of methanol HPLC grade and manually injected into one phenylhexyl column (Phenomenex, 21.2 mm×250 mm, 15 μm) connected to a preparative HPLC system (Waters, Prep LC2000). On-line monitoring of the purification process is performed at 228 nm on a tunable wavelength UV spectrophotometer (Waters, Model 486). Separation of the compounds is achieved under isocratic conditions which are acetonitrile:water (40:60) at a flow rate of 20 ml/min. Under those conditions, paclitaxel is eluted between 38.7 and 52.0 minutes. However, the collection of paclitaxel begins at 40.0 min. and ends at 45.5 minutes. As described above, the collected peak containing paclitaxel is evaporated in vacuo. The final yield of this overall purification process is 70% of paclitaxel (purity over 98.5%). FIG. 6A illustrates the content of the 65% pure paclitaxel used as raw material and FIG. 6B illustrates the content of the paclitaxel submitted to our purification process. Those chromatograms clearly demonstrate the high purity of the paclitaxel resulting from this purification process.

Therefore, it will be appreciated that the scope of this invention is defined by the claims appended hereto rather than by the specific embodiments which have been presented herein before by way of example.

What is claimed is:

1. A method for purifying a taxane, said method comprising the steps of:

(A) obtaining a crude taxane sample; and (B) subjecting said sample to chromatographic separation by passing said sample through a chromatographic column containing a phenylalkyl resin, wherein the alkyl portion of said phenylalkyl has from 4–10 carbon atoms; and thereafter (C) collecting a fraction of an eluant of said column containing said taxane.

2. The method of claim 1, wherein said taxane has the following molecular structure:

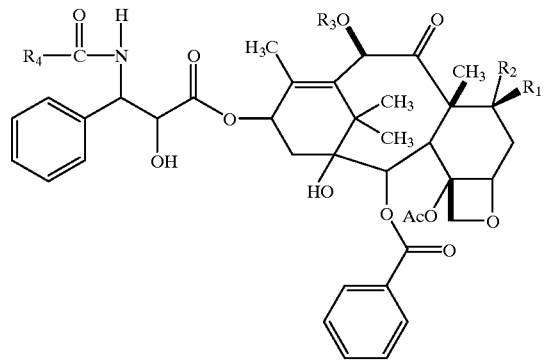

wherein $R^1$ and $R^2$ are independently selected from the group consisting of hydrogen and hydroxyl;

wherein $R^3$ is independently selected from the group consisting of hydrogen and acetyl; and wherein $R^4$ is independently selected from the group consisting of phenyl and $C_1$–$C_6$ alkyl.

3. The method of claim 1, wherein said taxane has the following molecular structure:

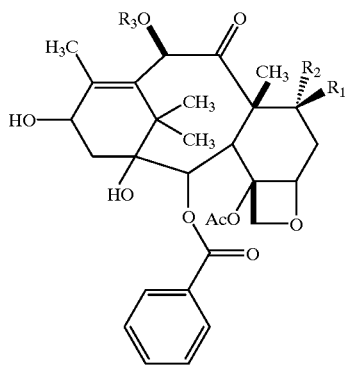

wherein $R^1$ and $R^2$ are independently selected from the group consisting of hydrogen and hydroxyl; and $R^3$ is independently selected from the group consisting of hydrogen and acetyl.

4. The method of claim 1, wherein said taxane has the following molecular structure:

wherein R¹ is selected from the group consisting of hydrogen and hydroxyl;

wherein R² is selected from the group consisting of hydrogen, hydroxyl and oxo.

5. The method of claim 1, wherein said taxane is selected from the group consisting of paclitaxel, 10-deacetyltaxol, 7-epi-taxol, cephalomannine, baccatin III, baccatin V, 7-epi-DAB, 10-deactylbaccatin III ("DAB") and 9-dihydro-13-acetylbaccatin III ("DHB").

6. The method of claim 1, wherein said taxane is from a vegetal source.

7. The method of claim 1, wherein said taxane is from a microbial source.

8. The method of claim 1, wherein said taxane is from a fungal source.

9. The method of claim 1, wherein said taxane is present at a concentration of at least 50% by weight relative to the entire crude sample exclusive of any extraction solvents or chromatography solvents.

10. A method for purifying a taxane, said method comprising the steps of:

(A) obtaining a crude taxane sample comprising said taxane at a concentration higher than 50% (by weight of said sample excluding extraction or chromatography solvents);

(B) solubilizing said sample;

(C) injecting said solubilized sample into a phenylhexyl chromatographic column connected to an HPLC preparative system;

(D) performing chromatographic separation by passing, through said column, a solvent that includes both organic and aqueous components;

(E) collecting a fraction of an eluant of said column containing said taxane;

(F) removing the solvent.

11. The method of claim 10, wherein chromatographic separation proceeds by an isocratic mode and said solvent is selected from the group consisting of:

(i) a mixture of methanol and water;

(ii) a mixture of acetonitrile and water; and (iii) a mixture of methanol, acetonitrile and water.

12. The method of claim 11, wherein water in subparagraphs (i)–(iii) is present at a concentration from 25–60% by weight of all solvent;

wherein methanol in subparagraphs (i) and (iii) is present in a concentration from 45–75% by weight of all solvent; and wherein acetonitrile in subparagraphs (ii)–(iii) is present at a concentration from 1–45% by weight of all solvent.

13. The method of claim 12, wherein the solvents are removed by evaporating organic solvent in vacuo followed by freeze-drying the aqueous phase.

14. The method of claim 10, wherein said taxane has the following molecular structure:

wherein R¹ and R² are independently selected from the group consisting of hydrogen and hydroxyl;

wherein R³ is independently selected from the group consisting of hydrogen and acetyl; and wherein R⁴ is independently selected from the group consisting of phenyl and C₁–C₆ alkyl.

15. The method of claim 10, wherein said taxane has the following molecular structure:

wherein R¹ and R² are independently selected from the group consisting of hydrogen and hydroxyl; and R³ is independently selected from the group consisting of hydrogen and acetyl.

16. The method of claim 10, wherein said taxane has the following molecular structure:

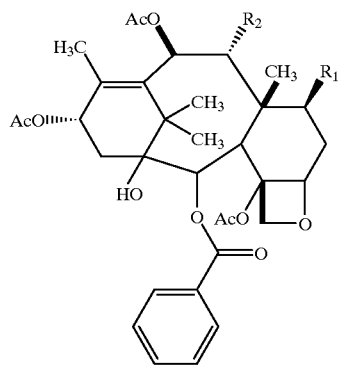

wherein R¹ is selected from the group consisting of hydrogen and hydroxyl; and wherein R² is selected from the group consisting of hydrogen, hydroxyl and oxo.

17. The method of claim 10, wherein said taxane is selected from the group consisting of paclitaxel, 10-deacetyltaxol, 7-epi-taxol, cephalomannine, baccatin III, baccatin V, 7-epi-DAB, 10-deactylbaccatin III ("DAB") and 9-dihydro-13-acetylbaccatin III (:DHB").

18. The method of claim 10, wherein said taxane is from a vegetal source.

19. The method of claim 10, wherein said taxane is from a microbial source.

20. The method of claim 10, wherein said taxane is from a fungal source.

21. The method of claim 1, wherein said resin is a phenylhexyl resin.

* * * * *